United States Patent
Nagar et al.

(10) Patent No.: US 11,408,878 B2
(45) Date of Patent: Aug. 9, 2022

(54) DYNAMIC PRODUCT LIFECYCLE PREDICTIONS BASED ON REAL-TIME PRODUCT QUALITY ANALYSIS

(71) Applicant: INTERNATIONAL BUSINESS MACHINES CORPORATION, Armonk, NY (US)

(72) Inventors: Raghuveer Prasad Nagar, Kota (IN); Jagadesh Ramaswamy Hulugundi, Bangalore (IN); Srikant Vitta, Bangalore (IN)

(73) Assignee: International Business Machines Corporation, Armonk, NY (US)

(*) Notice: Subject to any disclaimer, the term of this patent is extended or adjusted under 35 U.S.C. 154(b) by 385 days.

(21) Appl. No.: 16/575,740

(22) Filed: Sep. 19, 2019

(65) Prior Publication Data
US 2021/0088494 A1 Mar. 25, 2021

(51) Int. Cl.
| | | |
|---|---|---|
| *G01N 33/02* | (2006.01) | |
| *G01N 31/22* | (2006.01) | |
| *G06N 20/00* | (2019.01) | |
| *G06T 7/00* | (2017.01) | |

(52) U.S. Cl.
CPC ......... *G01N 33/02* (2013.01); *G01N 31/229* (2013.01); *G06N 20/00* (2019.01); *G06T 7/0002* (2013.01); *G06T 2207/10048* (2013.01); *G06T 2207/30128* (2013.01)

(58) Field of Classification Search
None
See application file for complete search history.

(56) References Cited

U.S. PATENT DOCUMENTS

| | | | |
|---|---|---|---|
| 6,327,576 B1 * | 12/2001 | Ogasawara | G06Q 10/087 705/22 |
| 6,549,135 B2 | 4/2003 | Singh | |
| 9,824,298 B1 * | 11/2017 | Krishnan Gorumkonda | G06Q 10/0832 |

(Continued)

FOREIGN PATENT DOCUMENTS

| | | |
|---|---|---|
| CN | 104330539 A | 2/2015 |
| WO | 2019050949 A1 | 3/2019 |

OTHER PUBLICATIONS

East Coast Daily, "Pocket size device to scan food", East Coast Daily, Jan. 4 [retrieved on Jul. 24, 2019], 2 pages, Retrieved from the Internet <URL: https://m.dailyhunt.in/news/india/english/east+coast+daily+eng-epaper-eeastco/pocket+size+device+to+scan+food-newsid-105513013>.

(Continued)

*Primary Examiner* — Leon Viet Q Nguyen
(74) *Attorney, Agent, or Firm* — Alexis N. Hatzis

(57) ABSTRACT

A method, computer system, and a computer program product for lifecycle prediction is provided. The present invention may include identifying a unit of a product that has been selected from a store bin. The present invention may include retrieving data from at least one connected Internet of Things (IoT) device and a connected infrared scanner. The present invention may include predicting a lifecycle of the identified unit. The present invention may include displaying the lifecycle on the at least one connected IoT device or the infrared scanner. The present invention may include determining whether the unit is added to a cart. The present invention may lastly include pushing the collected data to a point of sale for generating data at checkout.

17 Claims, 6 Drawing Sheets

(56) References Cited

U.S. PATENT DOCUMENTS

| | | | | |
|---|---|---|---|---|
| 2016/0169793 A1* | 6/2016 | Peng | ................... | G01N 21/474 |
| | | | | 250/214.1 |
| 2017/0052160 A1 | 2/2017 | Olsson | | |
| 2018/0211208 A1 | 7/2018 | Winkle | | |
| 2019/0152634 A1* | 5/2019 | Almogy | ............... | B65G 65/365 |
| 2020/0005230 A1* | 1/2020 | Brooks | ............ | G06Q 10/06315 |

OTHER PUBLICATIONS

Hertog, et al., "Shelf life modelling for first-expired-first-out warehouse management", Philosophical Transactions of The Royal Society, Jun. 13, 2014 [retrieved on Jul. 24, 2019], 15 pages, Royal Society Publishing, Retrieved from the Internet: <URL:https://www.ncbi.nlm.nih.gov/pmc/articles/PMC4006170/pdf/rsta20130306.pdf>.

Mell et al., "The NIST Definition of Cloud Computing", National Institute of Standards and Technology, Special Publication 800-145, Sep. 2011, 7 pages.

\* cited by examiner

DYNAMIC PRODUCT LIFECYCLE PREDICTIONS BASED ON REAL-TIME PRODUCT QUALITY ANALYSIS

BACKGROUND

The present invention relates generally to the field of computing, and more particularly to Internet of Things (IoT) devices and product lifecycles.

Every perishable product bought by consumers may have a lifecycle, and each product's lifecycle may consist of various changes and chemical compositions. For a perishable product, the lifecycle may be the length of time that a product may be stored before becoming unfit for use, consumption, and/or sale. The lifecycle may be affected by various factors which may include processing, handling, transportation, and/or environmental conditions. With many perishable products, a shelf life may be reflected by an expiry date (e.g., an expiration date) and/or a best-before (e.g., best-by, best if used by, use by, sell by) date. The expiry date may be a previously determined date after which the product should no longer be used. For many perishable products, the expiry date relates to food safety and may be reached when the product has exceeded an anticipated shelf life.

SUMMARY

Embodiments of the present invention disclose a method, computer system, and a computer program product for lifecycle prediction. The present invention may include identifying a unit of a product that has been selected from a store bin. The present invention may include retrieving data from at least one connected Internet of Things (IoT) device and a connected infrared scanner. The present invention may include predicting a lifecycle of the identified unit. The present invention may include displaying the lifecycle on the at least one connected IoT device or the infrared scanner. The present invention may include determining whether the unit is added to a cart. The present invention may lastly include pushing the collected data to a point of sale for generating data at checkout.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
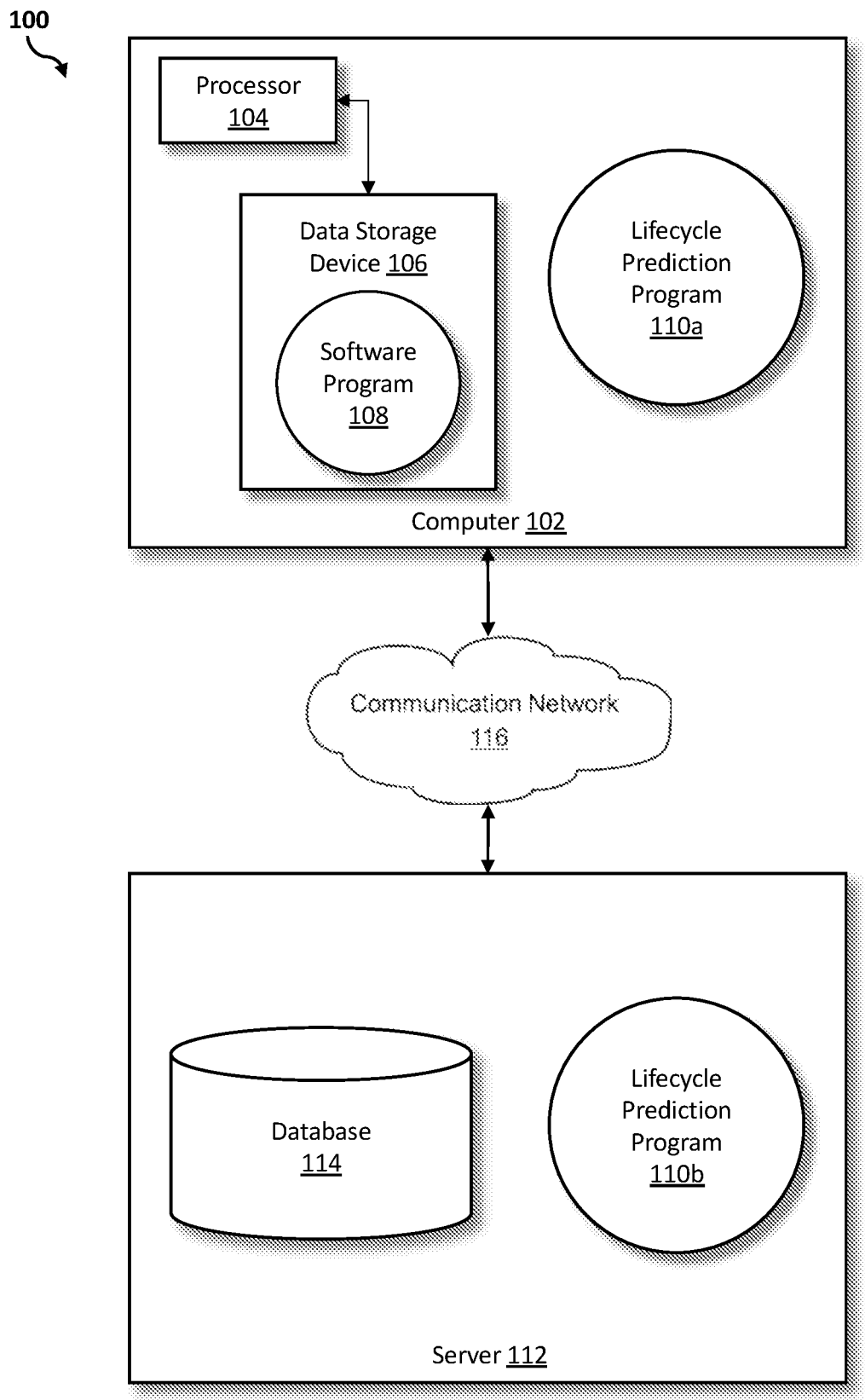
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for lifecycle prediction. As such, the present embodiment has the capacity to improve the technical field of Internet of Things (IoT) devices by providing consumer specific product lifecycle dates based on both a learning and analysis of a manner in which the consumer handles the product, as well as a real-time quality scan of the product itself. More specifically, the present invention may include identifying a unit of a product that has been selected from a store bin. The present invention may include retrieving data from at least one connected Internet of Things (IoT) device and a connected infrared scanner. The present invention may include predicting a lifecycle of the identified unit. The present invention may include displaying the lifecycle on the at least one connected IoT device or the infrared scanner. The present invention may include determining whether the unit is added to a cart. The present invention may lastly include pushing the collected data to a point of sale for generating data at checkout.

As previously described, every perishable product bought by consumers may have a lifecycle, and each product's lifecycle may consist of various changes and chemical compositions. For a perishable product, the lifecycle may be the length of time that a product may be stored before becoming unfit for use, consumption, and/or sale. The lifecycle may be affected by various factors which may include processing, handling, transportation, and/or environmental conditions. With many perishable products, a shelf life may be reflected by an expiry date (e.g., an expiration date) and/or a best-before (e.g., best-by, best if used by, use by, sell by) date. The expiry date may be a previously determined date after which the product should no longer be used. For many perishable products, the expiry date relates to food safety and may be reached when the product has exceeded the anticipated shelf life. Best-before dates, however, may refer to quality, not safety. For perishable products, the best-before date may refer to a period within which the product may still be safe to consume, but may begin to lose ripeness, flavor, texture, and/or other notorious qualities. After the best-before date, a product may be nearing the end of the product's shelf life.

Many produce and grocery products, such as fresh fruit and vegetables, may be picked, processed, and packed on the same day, in the same environment, and from the same orchards, yet many of the produce and grocery products may vary in physical nature and chemical composition. Thus, each item (i.e., unit) of produce and/or grocery may possess different a lifecycle date. Lifecycle dates listed for a whole batch may not be representative of individual units (e.g., item and/or units, wherein a specific product may be made up of one or more units of the product). Some fresh fruit and vegetables may even be sold without any lifecycle dates.

Attempting to judge when a unit may be at its peak quality and when a unit may have reached the end of its shelf life may be up to the consumer's discretion.

A consumer may have difficulty making a determination as to whether a unit may be at its peak quality and/or whether a unit may have reached the end of the unit's shelf life. Often, this may be difficult to evaluate manually as even individual units (i.e., products) in the same store bin, for example, may vary in ripeness and shelf life. Consumers may choose the most visually pleasing unit, even when other units may, in fact, be of better quality. Often times, imperfections on produce, for example, such as coloring variations and bruises do not affect the ripeness of the product, although such imperfections do affect a consumer's desire to purchase the unit. Leaving units which may be visually imperfect behind may contribute to food waste. Even after a unit may be bought by a consumer, the consumer may wait too long for a unit to ripen only to find the unit is no longer fit for consumption, thereby creating additional food waste. Therefore, it may be advantageous to, among other things, provide consumer specific product lifecycle dates based on both a learning and analysis of a manner in which the consumer handles the product, as well as a real-time quality scan of the product itself.

According to at least one embodiment, the present invention may identify that a consumer has selected a unit of a product from a store bin or other container. The consumer may select products unit by unit wherein a unit may be an individual instance of a given product, such as one apple, or a grouping of products, such as a bunch of bananas or a box of berries. The unit may be found in a physical store or in a virtual store which mirrors the product availability of a physical store. The store bin or other container may be a shelving unit, a carton, a pallet, or a display, among other things, upon which a product may be displayed and/or stored in a physical or virtual store.

According to at least one embodiment, the present invention may analyze data collected by a connected Internet of Things (IoT) device. The IoT device may be attached to or built into a store bin and/or other container located within the store. The collected data from the IoT device may include physical characteristics of the product and of each individual unit (e.g., unit of the particular product), which may include color, size (e.g., including height, length and depth dimensions), weight, breadth, a length dimension, and/or a height dimension, among other things. The IoT device may have a scale and/or camera which may be used to determine the product's physical characteristics. The IoT device may be capable of analyzing collected images. An infrared scanner may be further connected to and integrated with the IoT device and may thus be a component of a connected IoT system. An infrared scanner may have inbuilt image processing techniques for quality determination, as will be described in more detail below.

According to at least one embodiment, the present invention may scan the unit using a connected infrared scanner. The infrared scanner may use infrared light to collect information about a selected unit. Data collected by the infrared scanner may be processed by the infrared scanner to produce a thermal image. The infrared scanner may be connected to the IoT device, and the produced thermal images may be shared with and/or accessed by the connected IoT device. The infrared scanner may use infrared light for infrared spectroscopy to collect data characteristic of the selected unit and to measure the ripening, flavor, texture, and/or other notorious qualities of the selected unit. Different stages in a perishable product's (e.g., a food product's) lifecycle may have different chemical compositions. The absorbed wavelengths of light may permit the lifecycle prediction program to determine the chemical composition of the unit. Information gathered using the infrared scanner may be used to predict a lifecycle date of the product, and particularly of the selected unit.

According to at least one embodiment, the present invention may use learning and analysis to predict the lifecycle dates of a product and/or a unit. Specifically, supervised machine learning models may be used to predict the lifecycle dates of a product and/or a unit. A supervised machine learning model may utilize known input and output data in order to train a model and accurately predict future outputs. A supervised machine learning model may be implemented with the present system by feeding the model input data, used as training data, (e.g., a product type, one or more product feature(s) including but not limited to color, weight, dimension(s), and origin of the product, among other features, and an expected lifecycle) in order to teach the machine learning model how to predict a future lifecycle of the same or of a similar product.

Several subfields of machine learning models and/or algorithms may exist. Linear regression techniques may be suitable for use in conjunction with the present invention. However, the exact algorithm utilized may depend upon the product or unit being scanned. For example, the scanning of a bell pepper may utilize a different predicting function than, for example, a mango, due to seasonality and a projected freshness of a product at a particular time of year.

There may be many factors used to predict the lifecycle dates of a product and/or of a unit. In these instances, multi-linear regression techniques (e.g., multi-linear regression machine learning models), or multivariate linear regression techniques, may be utilized to handle n-dimensional predictions and learning, and may enable further accuracy. Linear regression may be a linear approach to modeling a relationship between a variable and one or more dependent variables. Multi-linear regression techniques may be used in instances where there is one dependent variable, and multivariate linear regression techniques may be used in instances where there is more than one dependent variable. A predicted lifecycle date may be one date (e.g., one variable) or a date range (e.g., 2 variables), and accordingly, both multi-linear regression techniques and multivariate linear regression techniques may be used.

Different factors (e.g., IoT device data, infrared scan data, image processing data, location information, and/or consumer information) may be assigned initial weights (e.g., by using a weighted least squares technique or an ordinary least squares technique, depending on a nature of the variance in the training data) which may be configured manually, and may also be dynamically adjusted based on the learning of the machine learning algorithms described above (e.g., the system auto adjusts any determined inaccuracy of a previous weight, based on continuous learning done by the machine learning model). A dynamic weight update may be automatically applied to the machine learning model.

The lifecycle dates may include one or more predicted dates indicating when the unit may be ripe, when the unit may be best-before, or when the unit may be expired. The predictions for the lifecycle dates may be derived based on various machine learning factors, including, but not limited to, collected unit data from an IoT device, infrared spectroscopy data, image processing of the selected unit, location information, and consumer information, among other things. Supervised machine learning algorithms, described above, may be used to predict lifecycle dates.

Image processing of the selected unit may comprise processing gathered images in an effort to understand any physical characteristics of the unit, which may include color, size, quantity, weight, length, breadth, and height, among other things.

Location information may include regional weather conditions, a unit's origin, and local government rules and regulations which may have affected the unit's condition, among other things.

Consumer information may include any information which may be obtained about the consumer (e.g., consumer profiling), including deriving individual preferences and relevant information included on public social media accounts, and/or obtaining information about a consumer's home location, home temperature, home pressure, and/or home humidity level, among other things. Consumer information may be gathered by accessing a connected consumer profile and/or by dynamically retrieving consumer information from connected IoT devices located in a consumer's home. Consumer information may be used to compute a handling pattern of a product and/or a unit before a consumer's purchase of the product and/or unit in order to provide a personalized expiration date (i.e., a personalized lifecycle) to the shopper. For example, if the consumer keeps his or her home at a temperature of 80 degrees Fahrenheit, and peaches that the consumer has picked up are known to ripen at a more rapid rate in higher temperatures, then the expiration date of the peaches may be dynamically adjusted and personalized to the consumer based on the consumer's known habits.

According to at least one embodiment, the present invention may display the lifecycle dates to the consumer. The lifecycle dates may include one or more predicted dates, including a date by which the unit may be ripe, a date by which the unit may be best-before, and/or a date by which the unit may be expired. The communication of a lifecycle date may include, but may not be limited to including, a digital display of a lifecycle date on a storage bin for the product or unit, a written (e.g., electronic) message sent to a consumer's phone and/or email account (e.g., based on a specified preference within a consumer profile), a voice over message leveraging natural language processing (NLP) techniques, and a digital display of a lifecycle date on an installed infrared scanner which may be located at the end of a store aisle.

The display of a predicted lifecycle date may also be displayed on a consumer's receipt at the time of checkout.

According to at least one embodiment, the present invention may determine when a unit is added to a consumer's cart. The lifecycle prediction program may recognize (e.g., based on collected images) a selected unit added to the consumer's cart, using the connected IoT devices, and may gather any previously predicted lifecycle information. Store containers, bins, totes, and/or trays, among other things, may be scanned by any connected IoT devices to determine which product(s) are being selected by the consumer. The lifecycle prediction program may then make a prediction as to the unit's current expected lifecycle.

According to at least one embodiment, the present invention may push unit generated data to a point of sale (POS) system for generating data at checkout. The POS system may generate an invoice which includes lifecycle dates for each unit in a consumer's cart. The invoice may be a receipt and/or a bill that the consumer receives after checkout. The invoice may be delivered to the consumer manually after checkout or through an email or text message, among other forms of delivery, depending on a configured consumer preference. An invoice generated by a POS system may be the last notification that a shopper may receive, and same may be generated at the time of checkout. There may be no further reminders to the consumer through any other methods of communication.

Alternatively, the lifecycle prediction program may keep track of which product(s) or unit(s) are added to a consumer's cart (e.g., in a consumer profile), and which of the product(s) or unit(s) the consumer purchased, as well as any predicted lifecycle dates. The lifecycle prediction program may send follow up messages to the consumer (e.g., a text message and/or email, depending on a specified consumer preference), for example, on a predicted expiry date, to remind the consumer that the product or unit is expiring.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and a lifecycle prediction program 110a. The networked computer environment 100 may also include a server 112 that is enabled to run a lifecycle prediction program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 3, server computer 112 may include internal components 902a and external components 904a, respectively, and client computer 102 may include internal components 902b and external components 904b, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the lifecycle prediction program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the lifecycle prediction program 110a, 110b (respectively) to provide consumer specific product lifecycle dates based on both a learning and analysis of a manner in which the consumer handles the product, as well as a real-time quality scan of the product itself. The lifecycle prediction method is explained in more detail below with respect to FIGS. 2A and 2B.

Referring now to FIG. 2, an operational flowchart illustrating the exemplary lifecycle prediction process 200 used by the lifecycle prediction program 110a and 110b according to at least one embodiment is depicted.

At 202, a unit selected by a consumer is identified. The unit may be a product from a store bin or other container. The consumer may select a product unit by unit, wherein a unit may be an individual instance of a given product or a grouping of units of the given product. Each time a unit is selected by the consumer, the lifecycle prediction program 110a, 110b may identify the selected unit.

For example, John may be a consumer shopping at a grocery store to buy food for the next week. John may have an account with the grocery store that is specific to John (e.g., the account includes any preferred brands and/or products that John may frequently purchase, as well as John's payment information and address). The grocery store may use the lifecycle prediction program 110a, 110b in the produce section at John's grocery store. John walks into the grocery store and picks up a McIntosh apple from a bin located in the produce section. Upon selecting the apple, the lifecycle prediction program 110a, 110b identifies that John has selected a single unit of the given product (i.e., a single McIntosh apple) from the store bin.

At 204, data for the unit is collected and read by an IoT device. The collected data may be comprised of physical characteristics of the unit which may include color, size, weight, length, breadth, and/or height of the unit. The physical characteristics may be collected by the IoT device which may have a camera and/or scale.

Continuing with the above example, the store bin containing McIntosh apples has an IoT device installed which includes a scale and a camera, to collect data for the lifecycle prediction program 110a, 110b. The data for the apple that John has picked up is collected by the IoT device. The collected data about the apple includes the apple's color, size, weight, and dimensions, including length, breadth, and height dimensions.

At 206, the unit is scanned using an infrared scanner. The infrared scanner may use infrared light to collect information about the selected unit. The infrared scanner may be connected to the IoT device. The infrared scanner may use infrared light for infrared spectroscopy to collect a spectrum of the selected unit and to measure the ripening, flavor, texture, and/or other notorious qualities of the selected unit. Different stages in a perishable product's (e.g., a food product's) lifecycle may have different chemical compositions. The absorbed wavelengths of light may permit the lifecycle prediction program 110a, 110b to determine the chemical composition of a unit. Information gathered using the infrared scanner may be used to predict a lifecycle date of the product, and particularly of the selected unit.

Continuing with the above example, an infrared scanner may scan the apple that John has selected. The infrared scanner may use infrared light for infrared spectroscopy to collect a spectrum of data concerning the selected apple.

At 208, one or more lifecycle dates for the unit are predicted. The lifecycle dates may include one or more predicted dates for when the unit may be ripe, when the unit may be best-before, or when the unit may be expired. The predictions for the lifecycle dates may be derived based on various machine learning factors, including, but not limited to, collected unit data from an IoT device, infrared spectroscopy data, image processing of the selected unit, location information, and consumer information, among other things. Image processing of the selected unit may comprise processing gathered images in an effort to understand any physical characteristics of the unit, which may include color, size, quantity, weight, length, breadth, and height, among other things. Location information may include regional weather conditions, a unit's origin, and local government rules and regulations which may have affected the unit's condition, among other things. Consumer information may include any information which may be obtained about the consumer (e.g., consumer profiling), including deriving individual preferences and relevant information included on public social media accounts, and/or obtaining information about a consumer's home location, home temperature, home pressure, and/or home humidity level, among other things. Consumer information may be gathered by accessing a connected consumer profile.

Continuing with the above example, the lifecycle prediction program 110a, 110b may use data collected from the IoT device and the infrared scanner, both which relate to the apple that John has selected, to predict the lifecycle dates for the selected unit.

As another example, Steve is shopping for fruit at a local grocery store. Steve walks over to a store bin and picks up a mango. Data about the mango is collected by the IoT device and an infrared scanner scans the selected mango to determine the chemical composition from infrared spectroscopy. The lifecycle prediction program 110a, 110b also uses the collected data, along with location information, to predict one or more lifecycle dates for the selected mango. The mango that Steve selected was sourced from India, where there had been excess rain during the growing season. Using the collected data from the IoT device, infrared scanner, and location information, the lifecycle prediction program 110a, 110b predicts that the mango is already ripe today and will stay ripe for only 1 more day.

At 210, the lifecycle dates are displayed for the consumer. The lifecycle dates may include one or more predicted dates, including a date by which the unit may be ripe, a date by which the unit may be best-before, and/or a date by which the unit may be expired. The communication of a lifecycle date may include, but may not be limited to including, a digital display of a lifecycle date on a storage bin for the product or unit, a written message sent to a consumer's phone and/or email account, a voice over message leveraging natural language processing (NLP) techniques, and a digital display of a lifecycle date on an installed infrared scanner which may be located at the end of a store aisle.

Continuing with the example concerning John, the lifecycle prediction program 110a, 110b displays the lifecycle dates to John using a digital screen above the store bin. From the connected digital screen of the lifecycle prediction program 110a, 110b, John gathers that the apple is currently ripe and will last for another 5 days.

As another example, Mary goes shopping at a supermarket store. Mary is a member of the supermarket and has a consumer account with the store. Mary needs to buy avocados to make guacamole later that week. At the store, Mary picks up an avocado from the store bin. Data about the avocado is collected by a connected IoT scale and camera, and an infrared scanner scans the avocado to determine the avocado's chemical composition and ripeness. The lifecycle prediction program 110a, 110b also has access to Mary's consumer information, including individual preferences, social media, and Mary's home information. Mary's consumer information reveals that Mary tends to keep her house at a relatively cold temperature. Using the collected data from the IoT device, infrared scanner, and consumer information about Mary, the lifecycle prediction program 110a, 110b predicts that the avocado has already passed its peak ripeness but is still fit for consumption for 2 more days. The lifecycle prediction program 110a, 110b sends this information to Mary in a text message, which is a preference configured by Mary in Mary's consumer account with the store. Mary decides she does not want this avocado and instead selects another avocado from the store bin. Data about the second selected avocado is collected by the IoT devices and an infrared scanner scans the second selected avocado. Using the collected data from the IoT devices, the infrared scanner, and the consumer information gathered about Mary, the lifecycle prediction program 110a, 110b predicts that the avocado will be ripe in 3 days and will stay ripe for 2 days after that. The lifecycle prediction program 110a, 110b sends this information to Mary in a text message. Mary decides she wants to buy the second selected avocado based on this information.

At 212, the lifecycle prediction program 110a, 110b determines whether the consumer added the unit to a shopping cart. If the lifecycle prediction program 110a, 110b determines that the selected unit is added to a consumer's cart, then at 214, unit data is pushed to a POS for generating data at checkout. Continuing with the example concerning John, he decides to add the apple to his shopping cart and the lifecycle prediction program 110a, 110b determines that John has added the apple to his cart.

As another example, Jack goes shopping at a grocery store after work. Jack picks up a tomato from the store bin. The lifecycle prediction program 110a, 110b identifies a unit has been selected by a consumer and collects data about the unit by an IoT device connected to the store bin. The collected data concerning the selected tomato includes the tomato's color, weight, and dimensions. Jack walks over to an installed infrared scanner at the end of an aisle a few feet away and scans the tomato. The installed infrared scanner collects the infrared spectrum of the tomato and uses the spectrum to determine the tomato's chemical composition and ripeness. The lifecycle prediction program 110a, 110b, uses the collected data from the IoT device and infrared scanner to predict the lifecycle dates for the tomato and displays this information to Jack to read on the digital screen of the infrared scanner. Jack reads the predicted date and adds the tomato to his cart before he continues shopping. The lifecycle prediction program 110a, 110b determines that Jack has added the tomato to his cart as he is likely intending on purchasing the tomato.

At 214, data for the unit is pushed to a point of sale (POS) system. The POS system may generate an invoice which includes lifecycle dates for each unit in the cart. The invoice may be a receipt and/or bill that the consumer receives after checkout. The invoice may be delivered to the consumer manually after checkout or through an email or text message, among other forms of delivery, depending on a configured consumer preference.

Continuing with the example concerning John, the lifecycle prediction program 110a, 110b pushes the predicted lifecycle dates to the POS system of the grocery store. When John finishes shopping and checks out, the predicted lifecycle dates for the apple are printed next to the item listing on the receipt.

As another example, Sally goes shopping weekly for groceries. Often times, Sally has to throw away food waste that she forgets about or that goes bad too quickly. This week, when Sally goes to her usual grocery store with which she has a consumer account, she finds that the store has begun using the lifecycle prediction program 110a, 110b in the produce section. On her shopping list for the week Sally plans to buy bananas and lettuce. Sally goes to pick up the bananas. She selects a bunch of 3 bananas. The lifecycle prediction program 110a, 110b identifies, using a connected IoT camera device, that the bananas have been selected by a consumer and collects data about the bunch including color, size, quantity, and weight. The built-in infrared scanner then scans the bunch of bananas using infrared light to collect information about the selected bunch of bananas. Using the collected data from the IoT device and infrared scanner, the lifecycle prediction program 110a, 110b predicts that the bananas will be ripe for another 4 days. The lifecycle prediction program 110a, 110b informs Sally of the predicted lifecycle using a voice over system connected to the IoT device, Sally's preferred method of communication. Sally decides to buy the bananas and adds them to her cart. Sally then walks over to the lettuce and selects a head of lettuce from the store bin. The lifecycle prediction program 110a, 110b identifies that a head of lettuce has been selected by a consumer and collects data about the lettuce including color, size, quantity, and weight. The built-in infrared scanner then scans the head of lettuce using infrared light to collect a spectrum of the item. Using the collected data from the IoT device and infrared scanner, the lifecycle prediction program 110a, 110b predicts that the head of lettuce will be ripe for another 1 day. The lifecycle prediction program 110a, 110b informs Sally of the predicted lifecycle using a voice over system connected to the IoT device. Sally decides to put the head of lettuce back and selects a different head of lettuce. For the second selected head of lettuce, the lifecycle prediction program 110a, 110b predicts, using data collected from the IoT device and infrared scanner, and informs Sally through voice over that the lettuce should be ripe for the next 5 days. Sally decides to buy this head of lettuce and adds it to her cart. The lifecycle prediction program 110a, 110b determines that Sally has added the lettuce to her cart and pushes the predicted lifecycle dates to the POS system based on Sally's consumer account. When Sally checks out, she has the option to select an email receipt, which will include the predicted lifecycle dates of the products Sally selected. After checkout, Sally receives an email and finds the predicted lifecycle dates listed next to each respective item.

If, at 212, the lifecycle prediction program 110a, 110b determined that the unit was not added to a consumer's cart and may have been returned to the store bin, then the lifecycle prediction program 110a, 110b ends.

Figure 2A:
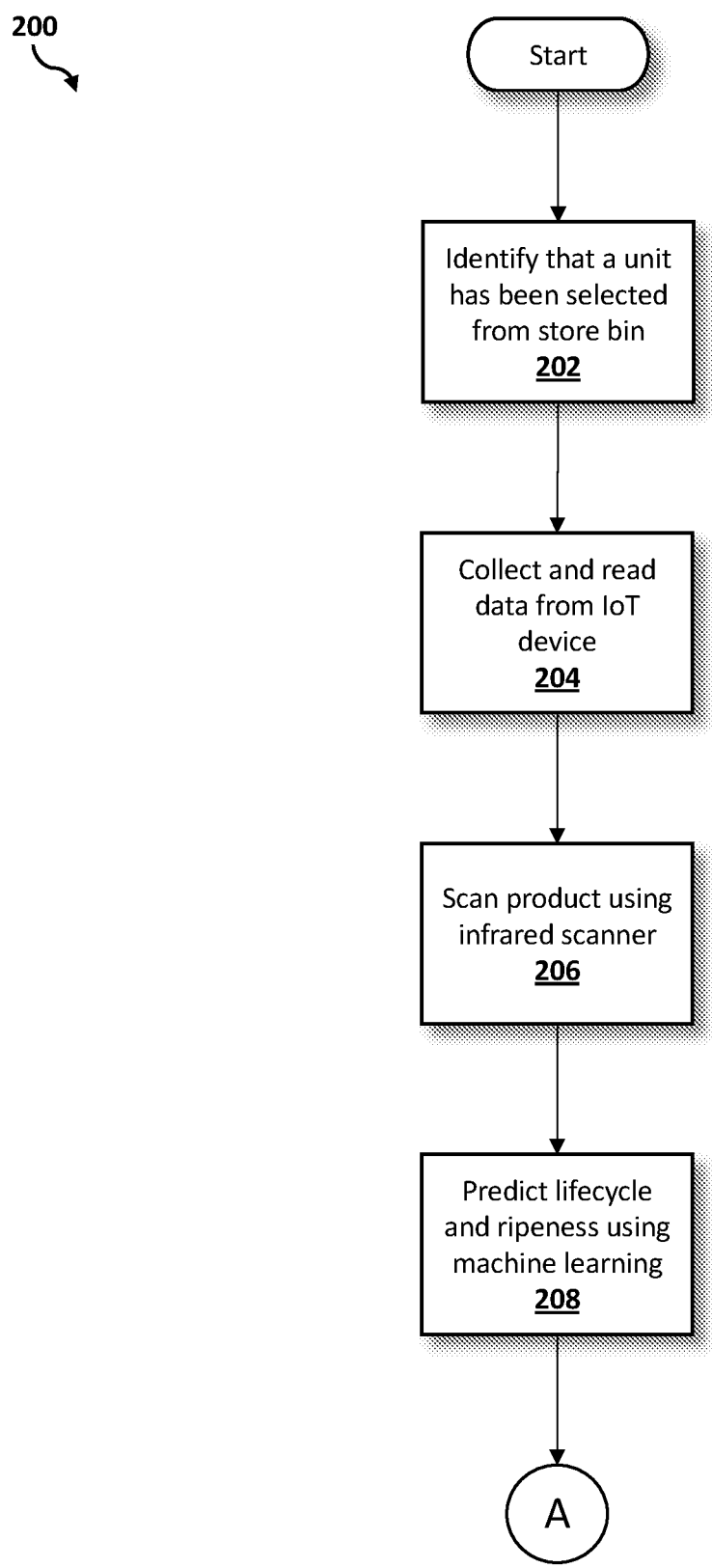
FIGS. 2A and 2B are an operational flowchart illustrating a process for lifecycle prediction according to at least one embodiment.
Figure 2B:
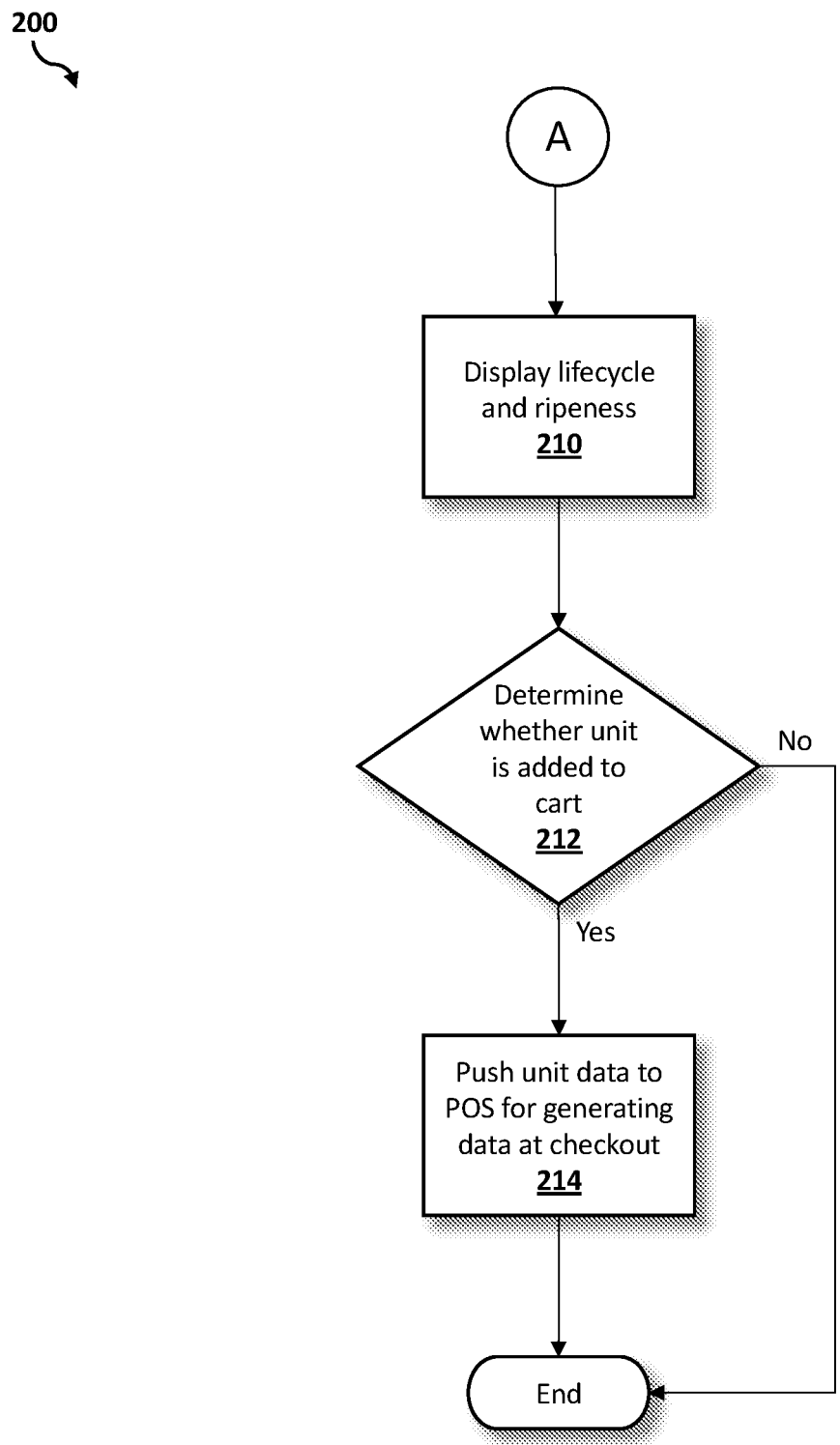

It may be appreciated that FIGS. 2A and 2B provide only an illustration of one embodiment and do not imply any limitations with regard to how different embodiments may be implemented. Many modifications to the depicted embodiment(s) may be made based on design and implementation requirements.

According to at least one alternate embodiment, the present invention may provide a recommendation and/or instruction relating to storage of a product and/or unit. This may include, but is not limited to including, making the consumer aware of a number of days during which the product or unit may remain ripe if refrigerated, as well as an optimal refrigeration temperature and method of storage (e.g., kept in plastic, removed from plastic, stored in a bin).

Figure 3:
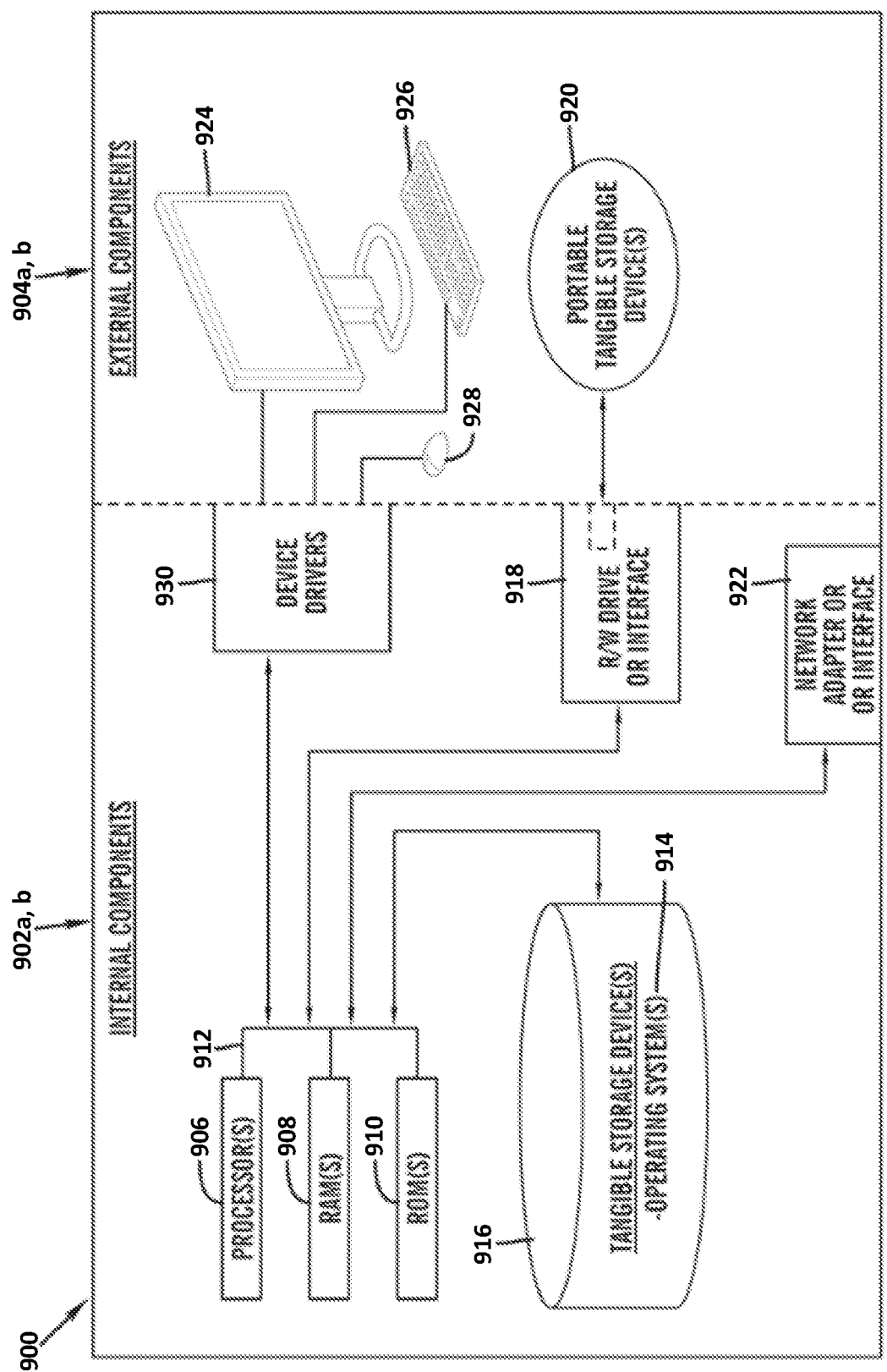
FIG. 3 is a block diagram of internal and external components of computers and servers depicted in FIG. 1 according to at least one embodiment.

FIG. 3 is a block diagram 900 of internal and external components of computers depicted in FIG. 1 in accordance with an illustrative embodiment of the present invention. It should be appreciated that FIG. 3 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902a, b and external components 904a, b illustrated in FIG. 3. Each of the sets of internal components 902a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108, and the lifecycle prediction program 110a in client computer 102, and the lifecycle prediction program 110b in network server 112, may be stored on one or more computer-readable tangible storage devices 916 for execution by one or more processors 906 via one or more RAMs 908 (which typically include cache memory). In the embodiment illustrated in FIG. 3, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the lifecycle prediction program 110a and 110b can be stored on one or more of the respective portable computer-readable tangible storage devices 920, read via the respective R/W drive or interface 918 and loaded into the respective hard drive 916.

Each set of internal components 902a, b may also include network adapters (or switch port cards) or interfaces 922 such as a TCP/IP adapter cards, wireless wi-fi interface cards, or 3G or 4G wireless interface cards or other wired or wireless communication links. The software program 108 and the lifecycle prediction program 110a in client computer 102 and the lifecycle prediction program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the lifecycle prediction program 110a in client computer 102 and the lifecycle prediction program 110b in network server computer 112 are loaded into the respective hard drive 916. The network may comprise copper wires, optical fibers, wireless transmission, routers, firewalls, switches, gateway computers and/or edge servers.

Each of the sets of external components 904a, b can include a computer display monitor 924, a keyboard 926, and a computer mouse 928. External components 904a, b can also include touch screens, virtual keyboards, touch pads, pointing devices, and other human interface devices. Each of the sets of internal components 902a, b also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
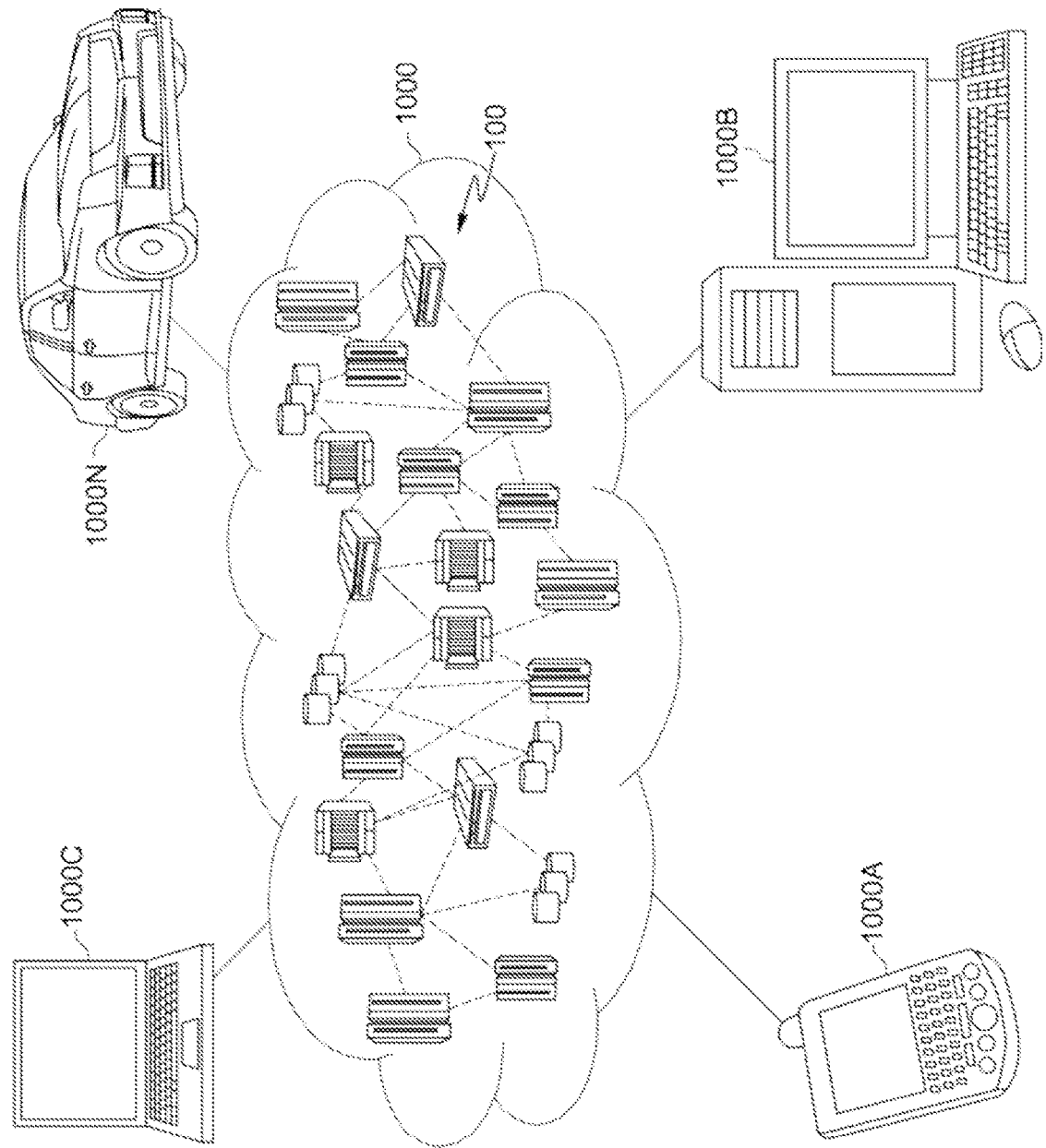
FIG. 4 is a block diagram of an illustrative cloud computing environment including the computer system depicted in FIG. 1, in accordance with an embodiment of the present disclosure.

Referring now to FIG. 4, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 4 are intended to be illustrative only and that computing nodes 100 and cloud computing environment 1000 can communicate with any type of computerized device over any type of network and/or network addressable connection (e.g., using a web browser).

Figure 5:
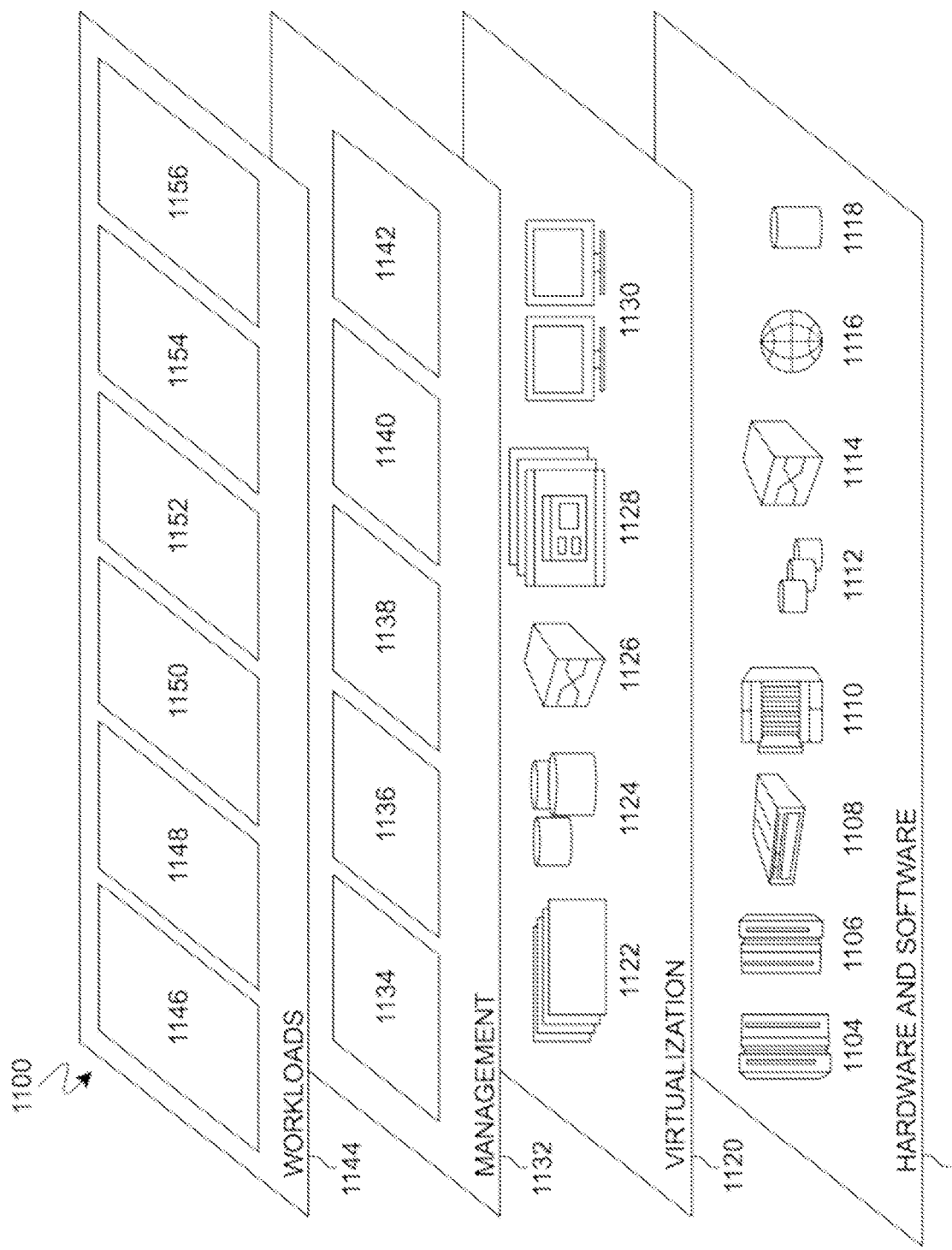
FIG. 5 is a block diagram of functional layers of the illustrative cloud computing environment of FIG. 4, in accordance with an embodiment of the present disclosure.

Referring now to FIG. 5, a set of functional abstraction layers 1100 provided by cloud computing environment 1000 is shown. It should be understood in advance that the components, layers, and functions shown in FIG. 5 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and lifecycle prediction 1156. A lifecycle prediction program 110a, 110b provides a way to provide consumer specific product lifecycle dates based on both a learning and analysis of a manner in which the consumer handles the product, as well as a real-time quality scan of the product itself.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for lifecycle prediction, the method comprising:
- identifying a unit of a product that has been selected from a store bin;
- retrieving data from at least one connected Internet of Things (IoT) device and a connected infrared scanner;
- predicting a lifecycle of the identified unit using a multi-linear regression technique, wherein the lifecycle is a personalized lifecycle of the identified unit based on more than one factor, wherein each factor is assigned a weight, and wherein the weight of each factor is dynamically adjusted;
- displaying the lifecycle on the at least one connected IoT device or the infrared scanner;
- determining whether the unit is added to a cart; and
- pushing the retrieved data to a point of sale for generating data at checkout.

2. The method of claim 1, wherein retrieving data from at least one connected Internet of Things (IoT) device and the connected infrared scanner further comprises:
- collecting one or more images, from an IoT camera, depicting color, size, and quantity information of the identified unit;
- collecting one or more thermal images, from the connected infrared scanner, depicting ripening, flavor, and texture of the identified unit; and
- analyzing the retrieved data.

3. The method of claim 1, wherein the multi-linear regression technique is a supervised machine learning model, implemented with a plurality of known input and output data, to predict the personalized lifecycle of the identified unit.

4. The method of claim 1, wherein displaying the lifecycle on the at least one connected IoT device or the infrared scanner further comprises:
- digitally displaying the lifecycle on a storage bin for the identified unit or the infrared scanner; and
- sending, based on a predefined user preference, an electronic message to a user.

5. The method of claim 1, wherein determining whether the unit is added to the cart further comprises:
- retrieving, from the at least one connected Internet of Things (IoT) device and the connected infrared scanner, images of the identified unit in the cart.

6. The method of claim 1, wherein pushing the retrieved data to the point of sale for generating data at checkout further comprises:
- generating an invoice which includes the lifecycle of the identified unit, wherein the invoice is a receipt, delivered electronically to a user upon checkout.

7. A computer system for lifecycle prediction, comprising:
- one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:
- identifying a unit of a product that has been selected from a store bin;
- retrieving data from at least one connected Internet of Things (IoT) device and a connected infrared scanner;
- predicting a lifecycle of the identified unit using a multi-linear regression technique, wherein the lifecycle is a personalized lifecycle of the identified unit based on more than one factor, wherein each factor is assigned a weight, and wherein the weight of each factor is dynamically adjusted;
- displaying the lifecycle on the at least one connected IoT device or the infrared scanner;
- determining whether the unit is added to a cart; and
- pushing the retrieved data to a point of sale for generating data at checkout.

8. The computer system of claim 7, wherein retrieving data from at least one connected Internet of Things (IoT) device and the connected infrared scanner further comprises:
- collecting one or more images, from an IoT camera, depicting color, size, and quantity information of the identified unit;
- collecting one or more thermal images, from the connected infrared scanner, depicting ripening, flavor, and texture of the identified unit; and
- analyzing the retrieved data.

9. The computer system of claim 7, wherein-the multi-linear regression technique is a supervised machine learning model, implemented with a plurality of known input and output data, to predict the personalized lifecycle of the identified unit.

10. The computer system of claim 7, wherein displaying the lifecycle on the at least one connected IoT device or the infrared scanner further comprises:
- digitally displaying the lifecycle on a storage bin for the identified unit or the infrared scanner; and
- sending, based on a predefined user preference, an electronic message to a user.

11. The computer system of claim 7, wherein determining whether the unit is added to the cart further comprises:
- retrieving, from the at least one connected Internet of Things (IoT) device and the connected infrared scanner, images of the identified unit in the cart.

12. The computer system of claim 7, wherein pushing the retrieved data to the point of sale for generating data at checkout further comprises:
- generating an invoice which includes the lifecycle of the identified unit, wherein the invoice is a receipt, delivered electronically to a user upon checkout.

13. A computer program product for lifecycle prediction, comprising:
- one or more non-transitory computer-readable storage media and program instructions stored on at least one of the one or more tangible storage media, the program instructions executable by a processor to cause the processor to perform a method comprising:
- identifying a unit of a product that has been selected from a store bin;
- retrieving data from at least one connected Internet of Things (IoT) device and a connected infrared scanner;
- predicting a lifecycle of the identified unit using a multi-linear regression technique, wherein the lifecycle is a personalized lifecycle of the identified unit based on more than one factor, wherein each factor is assigned a weight, and wherein the weight of each factor is dynamically adjusted;
- displaying the lifecycle on the at least one connected IoT device or the infrared scanner;
- determining whether the unit is added to a cart; and
- pushing the retrieved data to a point of sale for generating data at checkout.

14. The computer program product of claim 13, wherein retrieving data from at least one connected Internet of Things (IoT) device and the connected infrared scanner further comprises:

collecting one or more images, from an IoT camera, depicting color, size, and quantity information of the identified unit;

collecting one or more thermal images, from the connected infrared scanner, depicting ripening, flavor, and texture of the identified unit; and analyzing the retrieved data.

15. The computer program product of claim 13, wherein the multi-linear regression technique is a supervised machine learning model, implemented with a plurality of known input and output data, to predict the personalized lifecycle of the identified unit.

16. The computer program product of claim 13, wherein displaying the lifecycle on the at least one connected IoT device or the infrared scanner further comprises:

digitally displaying the lifecycle on a storage bin for the identified unit or the infrared scanner; and sending, based on a predefined user preference, an electronic message to a user.

17. The computer program product of claim 13, wherein determining whether the unit is added to the cart further comprises:

retrieving, from the at least one connected Internet of Things (IoT) device and the connected infrared scanner, images of the identified unit in the cart.

* * * * *